United States Patent [19]

Gee

[11] Patent Number: 5,550,124
[45] Date of Patent: Aug. 27, 1996

[54] USE OF PERIPHERAL-TYPE BENZODIAZPINE SITES FOR TREATMENT OF CNS TRAUMA OR DISEASE

[75] Inventor: Kelvin W. Gee, Hacienda Heights, Calif.

[73] Assignee: University of Southern California, Los Angeles, Calif.

[21] Appl. No.: 805,458

[22] Filed: Dec. 10, 1991

[51] Int. Cl.$^6$ ................................................. A61K 31/55
[52] U.S. Cl. .................................................... 514/221
[58] Field of Search ................................... 514/307, 221

[56] References Cited

U.S. PATENT DOCUMENTS

| | | | |
|---|---|---|---|
| 3,336,295 | 8/1967 | Sternbach et al. | 260/239.3 |
| 3,880,855 | 4/1975 | Juby et al. | 260/256.4 F |
| 4,005,099 | 1/1977 | Gall | 260/309 |
| 4,499,094 | 2/1985 | Dubroeucq et al. | 514/307 |
| 4,997,771 | 3/1991 | Barnett et al. | 436/501 |

OTHER PUBLICATIONS

Baldessarini, R. J., "Drugs and the Treatment of Psychiatric Disorders," in: Goodman & Gilman's The Pharmacological Basis of Therapeutics, Pergamon Press, N.Y., pp. 383–435 (1990).
Benavides et al., "The quantification of brain lesions with an $\omega_3$site ligand: a critical analysis of animal models of cerebral ischaemia and neurodegeneration," Brain Res. 522:275–289 (1990).
Bourdiol et al., "Increase in $\omega_3$(peripheral type benzodiazepine) binding sites in the rat cortex and striatum after local injection of interleukin-1, tumour necrosis factor-$\alpha$ and lipopolysaccharide," Brain Res. 543:194–200 (1991).
Braestrup, C. and Squires, R. F., "Specific benzodiazepine receptors in rat brain characterized by high affinity [$^3$H]diazepam binding", PNAS USA 74(9):3805–3809 (1977).
Drobinski et al., "Absence d'effet anti-ischémique d'qun antagoniste des récepteurs périphéques aux benzodiazépines PK 11195," Therapie 44:263–267 (1989).
Krueger et al., "Purification, Cloning, and Expression of a Peripheral–Type Benzodiazepine Receptor," Adv. Biochem. Psychopharmacol. 46:1–13 (1990).
Mizoule et al., "Opposite Effects of Two Ligands for Peripheral Type Benzodiazepine Binding Sites, PK 11195 and R05–4864," Life Sci. 36:1059–1068 (1985).
Muller et al., in: The Benzodiazepine Receptor: Drug Acceptor Only or a Physiologically Relevant Part of our Central Nervous System?, Cambridge Univ. Press, pp. 32, 33, 75 and 76 (1987).
Pellow, S. and File, S. E., "Characteristics of an Atypical Benzodiazepine, Ro 5–4864," Neurosci. Behav. Rev. 8:405–413 (1984).

Rall, T. W., "Hypnotics and Sedatives; Ethanol", in: Goodman and Gilman's The Pharmacological Basis of Therapeutics, Chapter 17, Pergamon Press, N.Y., pp. 345–382 (1990).
Schoemaker et al., "Specific High–Affinity Binding Sites for [$^3$H]Ro 5–4864 in Rat Brain and Kidney," J. Pharmacol. Exp. Ther. 225(1): 61–69 (1983).
Skerritt et al., "Diazepam and its Anomalous $\beta$–Chloro–derivative Ro 5–4864: Comparative Effects on Mouse Neurons in Cell Culture," Brain Res. 310:99–105 (1984).
Taupin et al., "Increase in IL–6, IL–1 and TNF levels in rat brain following traumatic lesion", J. Neuroimmunol. 42:177–186 (1993).
Wang et al., "Benzodiazepines that bind at peripheral sites inhibit cell proliferation," PNAS USA 81:753–756 (1984).
Wang et al., "Structural Requirements for the Binding of Benzodiazepines to Their Peripheral–Type Sites", Molec. Pharmacol. 25:349–351 (1984).
Demerlé–Pallardy et al., "Peripheral type benzodiazepine binding sites following transient forebrain ischemia in the rat: effect of neuroprotective drugs", Brain Res. 565:312–320 (Nov. 29, 1991).
Marana et al., "Cerebral Protection During Extracorporeal Circulation," Resuscitation 10:89–100 (1982).
"Differences in the mechanism of the antihypoxic action of benzodiazepine receptor agonists and muscimol," Biull Eksp Biol. Med. (USSR) 98(10):436–439 (1984).
Supplementary Partial European Search Report for EP 93 90 1476, issued Apr. 24, 1995. (6 pages).
Huff et al., Society for Neuroscience Abstracts, vol. 17, 1991.
Verrier et al., Aug. 1975, The Canadian Journal of Neurological Sciences, pp. 179–184.
Voll et al., Neurology 1991; 41:423–428.

Primary Examiner—Raymond Henley, III
Attorney, Agent, or Firm—Sterne, Kessler, Goldstein & Fox, P.L.L.C.

[57] ABSTRACT

It is a purpose of this invention to provide a means of treating various central nervous system (CNS) injuries to prevent or minimize damage to the CNS. A novel use has been found for some previously known compounds which are inhibitory agonists of the peripheral-type BZ receptors.

It is another purpose of this invention to provide a means of speeding the recovery of tissue damaged through injury to the CNS. The above described inhibitory agonists of the peripheral-type BZ receptors are useful for this purpose, and provide an easily administrable medication.

Additionally, a means is provided for screening for new compounds which will act as inhibitory agonists of the peripheral-type BZ receptors and therefore which can be used for treating CNS injuries and for speeding the recovery of tissue damaged through such injuries.

15 Claims, 6 Drawing Sheets

USE OF PERIPHERAL-TYPE BENZODIAZPINE SITES FOR TREATMENT OF CNS TRAUMA OR DISEASE

BACKGROUND OF THE INVENTION

A) Head Injury

Although the brain makes up only 2% of the entire body's weight, it receives 15% of the heart's output of blood and uses up 20% of the oxygen consumed by the body. An organ of this caliber is most vital to survival; within it are control centers for all the senses: sight, smell, touch, hearing, as well as control centers for breathing, hormonal release and all other basic homeostatic functions essential for survival. Damage which renders any portion of the brain dysfunctional can have a devastating effect on an animal's existence, causing neurological and medical problems, and often times death.

Different parts of the brain may be damaged in a wide variety of ways. Common causes of brain injury include vascular diseases and disorders, tumors, infections and actual head trauma.

Vascular disorders can be broken down into three main categories: (1) Problems involving hypoxia, ischemia, and infarction; (2) Intracranial hemorrhage; and (3) Hypertensive cerebrovascular disease.

The brain's dependence on a constant blood supply is of critical importance; it depends on oxygen-rich blood and glucose to function, and the brain is only able to store enough glucose to keep it running for one minute. After four minutes of blood deprivation, irreversible neuronal damage begins. There are two types of acute ischemic injury: (a) ischemic (hypoxic) encephalopathy occurs with a general decrease in cerebral blood flow and causes widespread damage; (b) cerebral infarction occurs following a severe drop or cessation in blood flow to one localized area of the brain. The latter is usually due to a local vascular occlusion and is what many people refer to as "stroke."

Vascular occlusions may be due to clots or arterial plaques but may be due to embolisms (usually from the heart) as well. Intracranial hemorrhage includes intracerebral, subarachnoid, and mixed intracerebral/subarachnoid hemorrhage. Intracerebral hemorrhage usually results from the rupture of aneurysms in hypertensive patients, causing a gradual neurologic deficit such as paralysis, sensory loss, coma or even death. The mortality rate is 40%. Subarachnoid hemorrhage is more superficial and occurs suddenly, usually with physical exertion. 20–50% of these patients die with the first rupture. Mixed intracerebral/subarachnoid hemorrhages are usually associated with arteriovenous malformations (AVM's), which are tangles of abnormal blood vessels both in superficial and deep brain structures. Patients with AVM's often experience seizures.

Hypertensive vascular disease can result in several brain injuries: atherosclerosis, which can lead to "stroke"; lacunae, which are small necrotic areas deep in the brain due to "small vessel stroke;" subcortical leukoencephalopathy, which is diffuse loss of deep white matter due to severe atherosclerosis and loss of perfusion; and finally hypertensive encephalopathy, which is usually seen in malignant (extremely severe) hypertension, and produces headache, drowsiness, vomiting, convulsions, damaged blood vessels, failure of autoregulation of cerebral blood flow, damage of the blood-brain barrier, cerebral edema, and possibly coma.

Brain tumors may either originate in the brain or metastasize to the brain from another part of the body, such as the lung, breast, or intestines. Complications of malignancy include brain degeneration, weakness, tingling and numbness, muscle spasms, dementia, fatigue, confusion, behavioral changes, chemical imbalances, and hemorrhages. Tumors can also impede the blood flow to the brain, resulting in ischemia.

Head trauma is a major cause of the ischemic condition in the brain, as well as causing other damage, such as direct tissue ruptures. In severe trauma, the skull, which is designed to protect the brain, travels faster than the brain on impact, and can actually act as a weapon and cause serious brain damage. In head trauma, the skull, dura and leptomeninges (tissue around the brain), blood-brain barrier (a series of membranes around brain arteries which keep unwanted, harmful molecules out of the brain) and finally the brain itself can all be injured. The four major groups of brain injuries include skull fractures, epidural hematoma, subdural hematoma, and deep brain parenchymal injuries.

Skull fractures can be deadly; the brain can be directly injured by penetrating broken bone fragments. Often, the broken skull causes the rupture of major arteries supplying the brain, usually the middle meningeal artery. Subdural hematomas occur frequently in head trauma due to the rupture of bridging veins in the brain, and usually occur on the side of the brain opposite the impact site. Parenchymal injuries, or injuries to the brain tissue itself, often occur following head trauma. In addition, shearing forces with impact often cause damage to the brian's white matter, a phenomenom referred to as diffuse axonal injury.

B) Chemical Injury

Drugs of abuse and misuse can cause serious brain injury as well. In addition, poisoning by heavy metals in many cases may damage the brain.

Amphetamines have been noted for their ability to cause widespread vascular damage to the brain. Aside from small artery occlusive disease, a condition known as periarteritis nodosa, or necrotizing angiitis, may develop. In this disorder, medium and small arteries of the brain develop aneurysms, sacculatioins, thromboses, and necrosis. In addition, amphetamine abuse has been linked with softening of the cerebral cortex and basal ganglia of the brain, subarachnoid hemorrhages, cerebral edema, ischemia, and infarction.

Cocaine is a potent vasoconstrictor, stimulant and anesthetic. It affects dopamine, norepinephrine, and serotonin neurons in the CNS by blocking the reuptake of these neurotransmitters, ultimately causing their depletion and destruction of dopaminergic pathways in the brain. Pituitary function, which depends on dopamine for some of its regulation, can become deranged, leading to hormonal imbalances throughout the body. Cocaine abusers run a high risk for cerebrovascular disease as well due to excessive vasoconstriction and oxygen depletion.

Nicotine, a component of tobacco, acts as a very potent vasoconstrictor. Carbon monoxide, also ingested by smoking, may impair CNS function by causing an increase in abnormal carboxyhemoglobin and depriving the brain of oxygen. Smokers carry an increased risk of stroke and/or cerebrovascular disease; they are more prone to subarachnoid hemorrhage, hypercoagulable states and cardiac arrhythmias.

Heavy metals can also impair brain function and in some cases lead to the ischemic state. For example, arsenic, commonly found in insecticides, fungicides and herbicides, affects the CNS by blocking aerobic respiration. Clinical symptoms from arsenic poisoning include delirium, coma, and seizures.

C) Neurodegenertive Diseases

A number of neurodegenerative diseases have been diagnosed and studied. Over-excitation of neurons, mediated mostly by glutamate, is believed to be an etiological factor in epilepsy, Alzheimer's Disease, Huntington's Chorea, and cerebral hypoglycemia and ischemia/hypoxia (Foster, A.C., et al, "Protection against N-methyl-D-aspartate receptor mediated neuronal degeneration in rat brain by 7-chlorokynurenate and 3-amino-1-hydroxypyrrolid-2-one, antagonists at the allosteric site for glycine," Eur. J. Neuroscience, 2:270–277(1990)).

D) Functioning of the Brain

In order to understand many of the effects of brain injuries, one must have a general understanding of how the brain operates under normal conditions.

Besides requiring 20% of the body's oxygen supply, the brain also consumes 25% of the body's glucose. The reason for this is the tremendous and constant need for the brain to produce energy. Blood flow to this region must be constant as well due to the brain's inability to store both glucose and oxygen. Under normal circumstances, the brain efficiently converts glucose to energy in the form of ATP by a process dependent on oxygen. The hypoxic brain, in an effort to save itself and still produce energy, relies on the inefficient process of anaerobic glucose metabolism. A by-product of this process is lactate, an acid, which sends a signal to the blood vessels that oxygen is running low. The vessels then dilate in an effort to compensate and supply the brain with more oxygen. If too much lactate accumulates, it impairs the cellular function of the neurons and makes them more susceptible to a second injury; that is, the cell is weakened and unable to handle toxins, chemical imbalances, or slight drops in oxygen which it can normally deal with. As an example, an already traumatized brain may undergo infarction with an ischemic insult that a normal healthy brain could easily tolerate. Furthermore, following severe concussion, there is a surge of adrenaline, which brings along with it an increase in blood glucose levels. Because blood flow is impaired at that time, there is a deficiency of oxygen and the brain reverts to anaerobic glucose metabolism, resulting in a huge surge in lactate, thus weakening the nerve cells.

Because the brain has a constant need for glucose and oxygen-rich blood, the rate of cerebral blood flow (CBF) must be carefully regulated. The brain has developed a delicate system to autoregulate CBF. It is usually remains within the range of 50–60 ml/minute/100 g of brain tissue, and is regulated by a variety of metabolic factors such as stretch of the smooth muscle cells in brain arterioles, changes in cerebral concentrations of oxygen and carbon dioxide ($CO_2$), blood pH, and nerve responses. Autoregualtion of CBF does not always work, however; when cerebral perfusion pressure exceeds 150 mm Hg and is less than 60 mm Hg, the system fails. After a traumatic brain injury, the sudden compensatory increase in arterial blood pressure exceeds the level at which autoregulation functions; paradoxical reactions and vasospasms begin to occur, clots form, and in general there is a decrease in CBF, hence causing the buildup of toxic metabolic waste products and lack of oxygen.

Another important consideration in brain injury is intracranial pressure (ICP). Two-thirds of patients with severe brain trauma also develop serious increases in ICP. The skull limits the area of space that the brain can occupy; hence traumatic injuries involving brain swelling (edema) or excess bleeding (hematomas) can compress the brain and cut off circulation to certain parts, impairing autoregualtion of CBF, causing permanent damage or even death. Hematomas must be drained as soon as possible to prevent this, and blood pressure must be kept reasonably low to reduce the amount of swelling in contusions.

Complications following brain trauma are often more devastating than the trauma itself. Neurological complications of brain injury include infection, swelling, epilepsy, delayed hemorrhage, amnesia, memory impairment, defects in movement, vision, sensation, and speech, paralysis, and possibly death. Other complications not related to the brain's neurological function include hormonal, cardiovascular, respiratory and gastrointestinal disorders, since control centers for these systems are located in the brain.

E) Treatments for Ischemia and Other CNS Injury

The main objective in the treatment of brain injuries is to minimize any neurological deficits and prevent the progression of further neurological damage. Cerebral ischemia, or stroke, is the most common cause of neurologic disability (Stein & Sabel, PHARMACOLOGICAL APPROACHES TO THE TREATMENT OF BRAIN AND SPINAL CORD INJURY, Plenum Press, New York, 1988). Stroke treatments currently available include calcium channel blockers, anticoagulation and antiplatelet therapy, surgery, and other supportive measures. The following is a description of currently available therapies for brain ischemia caused by strokes.

The principle behind calcium blockade is the finding that local ischemia brings about an increase in intracellular calcium ($Ca^{+2}$) (M. Fisher, MEDICAL THERAPY OF ACUTE STROKE, Marcel Dekker, Inc., New York, 1989). The abnormally high $Ca^{+2}$ concentration disrupts neuronal membrane pumps, and activates two classes of $Ca^{+2}$ dependent protein kinases, which in turn stimulate neurotransmitter release and the hydrolysis of arachidonic acid to prostaglandins and leukotrienes, both vasoactive substances. The excess of excitatory neurotransmitters may lead to cell death; arachidonic acid metabolites aggravate blood flow and stimulate the formation of damaging free radicals. Calcium excess also inhibits cellular respiration (Stein & Sabel, supra).

Calcium channel blockers slow the entry of $Ca^{+2}$ into cells. Promising drugs of this class prevent or reverse cerebral vasospasm and dilate cerebral blood vessels, leading to an improvement in cerebral blood flow. The problem with most drugs of this class is the systemic effect of vasodilation in organs other than the brain, which may occasionally end up drawing blood preferentially into these other organs rather than the brain. Other adverse systemic effects include abnormally slowed heart rates and "heart block," the blocking of electrical impulses which traavel through heart tissue; cardiac arrhythmias, congestive heart failure, may occur as well. Dizziness, positional or otherwise, may result from systemic hypotension (PHYSICIAN'S DESK REFERENCE, Medical Economics Co., Inc., Oradell N.J., 1990).

$Ca^{+2}$ blockers may also have deleterious effects on ischemic tissue. A study by Welch, et al., found that $Ca^{+2}$ blockers may prevent vasospasm in the absence of ischemia, but increase edema formation in the presence of ischemia (Welch, KMA and Barkley, GL, "Biochemistry and Pharmacology of cerebral ischemia, " Stroke 1:75–90, 1986). Some studies in rats have found the well-known $Ca^{+2}$ blocking drug Nifedipine to actually antagonize cerebral blood flow (Fisher, supra). Verapamil, another $Ca^{+2}$ blocker, has been found in some stroke studies to actually worsen focal ischemia by inappropriately increasing cerebral blood flow to nonischemic areas (Fisher, supra). In a study performed on dogs, Flunarizine, another $Ca^{+2}$ blocker, brought about no increase in cerebral blood flow or improvement in cerebral metabolism (Fisher, supra).

Nimodipine is a unique $Ca^{+2}$ blocker in that it has been shown in dogs to improve cerebral blood flow with little effect on peripheral vessels and blood pressure. No uniform benefit has been observed, however. One major problem with Nimodipine is that at low doses it acts as a $Ca^{+2}$ agonist rather than an antagonist, and actually worsens morbidity. It also may interfere with cellular energy metabolism and increase the susceptibility of tissue to ischemic damage by causing edema and cellular ionic imbalances (Fisher, supra).

Chelating agents, such as EDTA, are occasionally used to bind excess intracellular $Ca^{+2}$, but no well-characterized clinical studies of their use in stroke patients have been done (Stein & Sable, supra).

L-glutamate and L-aspartate, both acidic amino acids, act as excitatory neurotransmitters in the mammalian central nervous system. The major glutamate receptor subtype is known as the N-methyl-D-aspartate, or NMDA, receptor (Schoepp, DD, et al, "Neuroprotectant effects of LY 274614, a structurally novel systemically active competitive NMDA receptor antagonist," J. Neural Transmission, 85:131–143, (1991)). Located on the post-synaptic end of the neuron, the NMDA receptor possesses an ion channel as well as multiple regulatory/pharmacological domains, including the transmitter recognition site, to which glutamate and aspartate bind.

Binding of glutamate and other agonists to the NMDA receptor causes excitatory metabolic changes within the cell, including activation of intracellular second messenger proteins which contribute to irreversible neuronal injury, such as protein kinase C, calmodulin, and protein kinase II (Pohorecki, R., et al, "Ischemic brain injury in vitro: protective effects of NMDA receptor antagonists and calmidazolium," Brain Research, 528:133–137, (1990)).

Many researchers have attempted the use of various NMDA receptor antagonists to protect neurons from degeneration in various pathological states. For example, studies have been done on the NMDA competitive antagonist CGS 19755 and the noncompetitive antagonist MK-801 (Warner, M., et al, "Regionally selective effects of NMDA receptor antagonists against ischemic brain damage in the gerbil," J. Cerebral Blood Flow and Metabolism, 11:600–610 (1991)); and the non-competitive NMDA antagonist, dizocilpine (McCulloch, J., "Ischaemic Brain Damage—prevention with competitive and noncompetitive antagonists of N-methyl-D-aspartate receptors," Arznemittel-Forschung, 41:319–324 (1991)); the NMDA antagonist MK-801 (Dirnagl, U. et al, "Pre- and post-treatment with MK-801 but not pretreatment alone reduces neocortical damage after focal cerebral ischemia in the rat," Brain Research, 527:62–68 (19900; Haraldseth, O., et al, "The NMDA antagonist MK-801 improved metabolic recovery after 10 minutes global cerebral ischemia in rats measured with 31 phosphorous magnetic resonance spectroscopy," Acta Neurochirurgica, 106:32–36 (1990).

NMDA receptor antagonists are far from perfect drugs to treat brain injury. Adverse reactions are many and involve many organ systems. MK-801 and CPP have been found to induce respiratory depression and elevated $CO_2$ level. MK-801 increases blood pressure in rats and cats, while D-CPPene induces hypotension in cats. Noncompetitive antagonists such as MK-801 cause behavioral changes, including a psychotic-like response and diminished cognitive and mental status, even at doses needed for adequate anti-ischemic protection (Meldrum, Brian S., et al, EXCITATORY AMINO ACID ANTAGONISTS, Blackwell Scientific Publications, Oxford, 1991). Other general side effects of NMDA antagonists include central nervous system depression, hallucinations, tolerance development, abuse potential and possible direct neurotoxicity (Turski, L., "N-methyl-D-aspartat-rezeptorkomplex, " Arzenemittel-Forschung, 40:511–519 (1990)).

Preventing and dissolving thrombi, or clots, and maintaining blood viscosity and flow is an additional component of stroke therapy; however, reperfusion can lead to hemorrhage in the area of ischemic or infarcted tissue (Fisher, supra). Fibrinolysis, or the breakdown of already present clots, must be approached with caution; in excess it may actually promote cerebral hemorrhage (Stein & Sabel, supra). Antiplatelet therapy is used to prevent clot formation either postischemically in stroke patients or prophylactically in patients with a history of TIAs. Aspirin, indomethacin, sulfinpyrazone, and ticlopidine have been shown to inhibit platelet aggregation and prevent arachidonic acid from being metabolized into thromboxane A2, a potent platelet aggregator and vasoconstrictor (Zelenock, Gerald B., et al, CLINICAL ISCHEMIC SYNDROMES: MECHANISMS AND CONSEQUENCES OF TISSUE INJURY, The CV Mosby Company, St. Louis, 1990). Platelet anti-aggregants used post-stroke may help to reduce or prevent recurrence and improve microcirculation to ischemically impaired but viable brain tissue (Fisher, supra); however, they are not fast-acting and are not an absolute cure.

Inhibitors of prostaglandin synthesis, such as indomethacin have been found to significantly increase edema and decrease cerebral blood flow and carbon dioxide reactivity in ischemic baboons (Fisher, supra). Administration of prostaglandin I2 (PGI2) has also been attempted in stroke treatment. Unlike most prostaglandins, PGI2 promotes vasodilation and inhibits platelet aggregation. It is far from ideal, though, due to its extremely short half life (3 minutes) and its tendency to precipitate hypotension (Fisher, supra).

Other anticoagulant drugs include heparin and warfarin (Coumadin). These decrease the formation of intravascular thrombosis and embolism and prevent vascular obstruction, but are not widely used in stroke. These drugs carry with them the high risk of brain and/or systemic hemorrhage, and a rebound hypercoagulable state following cessation of warfarin or heparin treatment (Hart RG & Coull, BM, "Hypercoagulability following coumadin withdrawl," American Heart Journal, 106:169–170, 1983; Hart, RG, et al, "Rebound hypercoagulability, " Stroke, 13:527, 1982).

Pentoxifylline, or Trental, improves the oxygenation of ischemic tissues by decreasing blood viscosity by increasing the flexibility of rigid red blood cells, inhibiting platelet aggregation, and decreasing plasma levels of fibrinogen, a substance responsible for clot formation. In addition, it is a mild vasodilator. Many patients with cerebrovascular disease have elevated blood viscosity due to rigid red blood cells and increased tendency toward blood clots. Adverse side effects of Trental can include chest pain, dyspepsia, nausea, vomiting, dizziness, headache, tremor, anxiety, blurred vision, malaise, and others (PHYSICIAN'S DESK REFERENCE, Supra, at 1068–1069).

Another way to increase blood viscosity is by the use of hyperosmolar agents, such as mannitol, sorbitol or glycerol (Stein & Sabel, supra; Zelnock et al, supra). One problem with the use of mannitol and other similar agents is that they usually only provide temporary relief; furthermore, their discontinuation may result in severe rebound cerebral edema (Stein & Sabel, supra). They may disturb cerebral vascular autoregulation as well (Zelenock et al, supra).

Low molecular weight dextran (LMD) has been used for hemodilution as well, and although it decreases platelet aggregation, it exerts a negative effect on plasma viscosity and red blood cell flexibility (L'Etang et al., supra).

Pharmacological protection for stroke victims also involves the use of barbiturates such as pentobarbital and thiopental. Barbiturates decrease the cerebral metabolic rate and intracranial pressure and also may act to scavenge damaging free radicals released by ischemia and block cellular $Ca^{+2}$ influx (Zelnock et al, supra). Barbiturates inhibit CNS function by impairing excitatory neurotransmitter release and potentiating presynaptic inhibition by GABA. They must be administered within three hours of the onset of ischemia in order to be effective (Fisher, supra). Their use remains controversial; some animal experiments have found that in order to be effective, extremely high doses are needed (Corkill G et al., "Dose dependency of the post-insult protective effect of pentobarbital in the canine experimental stroke model, " Stroke, 9:10–12, 1978). Complications of barbiturate therapy include the possibility of respiratory depression and cardiac arrhythmias (Ruggieri S, et al, "Barbiturate treatment of acute stroke, " Adv. Neurology, 25:269, 1979). Discontinuation of barbiturate treatment may be followed by a fatal increase in intracranial pressure" (Yatsu, FM, et al., "Medical therapy of ischemic strokes, " Stroke, 2:1069–1083, 1986).

Another controversial acute stroke treatment involves the use of naloxone, an opiate (morphine) antagonist. In many clinical studies, its use has been shown to enhance the process of neurological recovery. Due to conflicting results and the fact that most studies have found naloxone to be ineffective in improving neurologic outcome, its use is not widespread. Furthermore, as dosage increases, naloxone tends to produce a harmful increase in systolic blood pressure and respiratory rate (Fisher, supra).

Steroids, such as dexamethasone are occasionally used in stroke treatment as well, to control edema. The use of dexamethasone in vasogenic edema with brain tumors has been successful, but conflicting reports exist as to its efficacy in the cytotoxic edema found in ischemia (Zelenock et al, supra). Many studies on the use of cortisone and dexamethasone for stroke treatment have shown no difference in morbidity or mortality in patients receiving treatment compared with controls (Dyken M, et al., "Evaluation of cortisone in the treatment of cerebral infarction, " JAMA, 162:1531–1534, 1956; Candelise L, et al ., "Therapy against brain swelling in stroke patients," Stroke, 6:353–356, 1975; Gilsanz V, et al., "Controlled trial of glycerol versus dexamethasone in the treatment of cerebral edema in acute cerebral infarction, " Lancet, 1:1049–1051, 1975). Furthermore, dexamethasone can cause serious exacerbations of diabetes mellitus (Norris JW, "Steroid therapy in acute cerebral edema," Archives of Neurology, 33:69–71, 1976). Perhaps most serious is the observation of Sapolsky & Pulsinelli, who in 1985 noted that ischemic injury was actually potentiated by steroids, perhaps via the release of excitatory neurotransmitters, leading to ATP depletion and an accumulation of intracellular $Ca^{+2}$ (Fisher, supra).

The neurotransmitter dopamine may be involved in stroke injury and recovery. Experimental studies have found dopamine blockade to inhibit recovery from strokes, especially in older animals. Another neurotransmitter which may be involved with stroke pathology is serotonin. Experiments have shown serotonin antagonists such as cinanserin and cyproheptadine to help preserve neurologic function when administered post-ischemia in animals. Tissue destruction and clinical deficits are diminished. The reason for this observed phenomenon is unclear, and this type of therapy is not widely used (Stein & Sabel, supra).

Surgical treatment of stroke most recently involves the use of percutaneous transluminal angioplasty (PCTA). PCTA has proven relatively successful; it is not perfect, however, and cannot be used immediately on a patient unless that patient is already hospitalized. Complications can include vessel dissection and occlusion if the vessel is overdistended by the balloon. Compression and occlusion of adjacent vessels may occur as well, due to balloons that are too long. Embolism may occur as well. Problems specific to carotid artery PCTA are linked to the fact that the carotid is especially inclined to spasm.

Recently, work using diazepam has shown it to be somewhat effective in treatment of cerebral ischemia. (R.A. Huff et al., "Diazepam following cerebral ischemia preserves CA1 pyramidal cells and $GABA_A$ receptors of the hippocampus," Soc. for Neuroscience Abstracts, 7:1079 (1991); C. L. Voll et al., "Postischemic seizures and necrotizing ischemic brain damage: neuroprotective effect of postischemic diazepam and insulin," Neurology 41:423–428 (1991)).

F) Peripheral-Type Benzodiazpine Receptors

Benzodiazepines (BZs) are a family of compounds which include drugs used as tranquilizers, sleeping aids, muscle relaxants, and anti-convulsants, and include Valium, Halcion, and Xanax. In 1977, specific BZ receptors were discovered in the neuronal cell membranes in the brain. S. H. Snyder, DRUGS AND THE BRAIN (1986) Scientific American Books, Inc., pp. 167–169. At that time, no naturally occurring agonists or antagonists of the BZ receptors were known. Although the question has not yet been completely answered, several discoveries involving the BZ receptor and its function have been made since 1977.

One major finding was that GABA, an inhibitory neurotransmitter which slows the neuron's rate of firing, stimulated the binding of BZs to the BZ receptor, and likewise, BZs stimulated the binding of GABA to its receptor. Each enhanced the neuronal inhibitory action of the other, by increasing the ease of opening of the neuron's Chloride (Cl) channel and increasing Cl conductance, thus decreasing the activity of the nerve cell. It has now been shown that there exist receptors, originally found in the brain and therefore termed "central-type" BZ receptors, which are associated with a receptor complex which has binding sites for $GABA_A$, BZs, barbiturates and convulsants. This complex is called the $GABA_A$ receptor-chloride ionophore complex (GRC), and is located near the neuron's Cl channel. When both GABA and BZ bind to their respective receptors, the Cl channel opens with greater frequency, thus allowing for a great influx of Cl into the cell and diminished neuronal activity. Convulsants such as picrotoxin cause the opposite effect. S. H. Snyder, supra, pp. 174–176.

In 1977, researchers found that BZ receptors were present not only in the brain and spinal cord (CNS), but in other organs, such as the heart, as well. W. E. Muller, THE BENZODIAZEPINE RECEPTOR: DRUG ACCEPTOR ONLY OR A PHYSIOLOGICALLY RELEVANT PART OF OUR CENTRAL NERVOUS SYSTEM (1987), Cambridge University Press, pp. 32–33. These receptors have a different substrate specificity; i.e., they bind some BZ derivatives with a different affinity than do the central-type receptors, and are believed to modulate a calcium ($Ca^{+2}$) channel as well. In addition to binding BZ derivatives, these receptors have been found to bind various organic compounds such as isoquinoline carboxamides, quinoline propanamides, imidazopyridines, porphyrins, thiazide diuretics, and others. Krueger, et al., "Purification, Cloning, and Expression of a Peripheral-Type Benzodiazepine Receptor," in Biggio and Costa, eds., GABA AND BENZODIAZEPINE RECEPTOR SUBTYPES,pp. 1–14 (1990).

These so-called "peripheral-type" BZ receptors have also been found in the CNS as well, but with a different distribution than the central-type BZ receptors. W. E. Muller, supra, pp. 33, 75. Both types are found in high density in the olfactory bulb, but unlike central-type BZ receptors, peripheral-type BZ receptors also are concentrated in the pineal gland, posterior pituitary, and choroid plexus. Furthermore, patients with Alzheimer's Disease have been found to have an elevated amount of peripheral-type BZ receptors in the cortex of their frontal lobes, and patients suffering from Huntington's Chorea have an abnormally high concentration of these receptors in the putamen, compared to patients without these diseases. W. E. Muller, supra at 75-76; D. Diorio et al., "Peripheral benzodiazepine binding sites in Alzheimer's disease frontal and temporal cortex," Neurobiol. Aging, 12:255–258 (1991).

The peripheral-type BZ receptors have been cloned in order to allow further study of the pharmacological actions of BZs and other molecules on these receptors. Krueger, et al., supra.

Recently, evidence has developed which suggests that the number of peripheral-type BZ receptors is directly related to neurological trauma, and may be used as a marker in rodent brains for excitotoxic, ischemic and proliferative damage. Benavides et al., "The quantification of brain lesions with an $\omega_3$ site ligand: a critical analysis of animal models of cerebral ischaemia and neurodegeneration, " Brain Res. 522:275–289 (1990). Additionally, it has been demonstrated that the number of peripheral-type BZ receptor sites increases in the brain when certain cytokines are administered locally. F. Bourdiol, et al., "Increase in $\omega_3$ (peripheral type BZ) binding sites in the rat cortex and striatum after local injection of interleukin-1, tumor necrosis factor-$\alpha$ and lipopolysaccharide," Brain Research 543:194–200 (1991). The data produced by these researchers suggests that the increased number of these peripheral-type receptors may be due to increased numbers of glial cells at the injection site.

Other recent work has shown that the binding of BZs at peripheral-type sites inhibits proliferation of a number of cell types. J. K. T. Wang et al., "Benzodiazepines that bind at peripheral sites inhibit cell proliferation," Proc. Natl. Acad. Sci. (USA), 81:753–756 (1991).

Several theories have been advanced for treatment of brain trauma through the administration of various compounds. Several groups have suggested that diazepam acts to prevent damage to the brain by decreasing excitatory neurotransmission at the $GABA_A$ receptor-chloride ionophore complex (GRC). C. L. Voll et al., supra; R. A. Huff et al., spra. However, no evidence has been produced to show that BZs which bind solely to the excitation-modulating central-type BZ receptors can have any positive effect on cerebral ischemia.

However, studies done on compounds other than diazepam which bind to the peripheral-type BZ receptors have found them to be ineffective in treating cardiac ischemia. G. Drobinski, et al., "Absence d'effet anti-ischémique d'un antagoniste des récepteurs périphériques aux benzodiazepines PK 11195, " Therapie, 44:263–267 (1989).

Another theory advanced is that the treatment of head injury is through the prevention of excess oxidation at the site of injury. Jacobsen, E. J., et al., "Novel 21-aminosteroids that inhibit iron-dependent lipid peroxidation and protect against central nervous system trauma," J. Med. Chem., 33:1145–1151 (1990). However, the active compounds of the present invention do not act in this manner.

BRIEF DESCRIPTION OF THE DRAWINGS

The present invention may be better understood and its advantages appreciated by those skilled in the art by referring to the accompanying drawings wherein.

SUMMARY OF THE INVENTION

It is a purpose of this invention to provide a means of treating various central nervous system (CNS) injuries to prevent or minimize damage to the CNS. A novel use has been found for some previously known compounds which are inhibitory agonists of the peripheral-type BZ receptors.

It is another purpose of this invention to provide a means of speeding the recovery of tissue damaged through injury to the CNS. The above described inhibitory agonists of the peripheral-type BZ receptors are useful for this purpose, and provide an easily administrable medication.

Additionally, a means is provided for screening for new compounds which will act as inhibitory agonists of the peripheral-type BZ receptors and therefore which can be used for treating CNS injuries and for speeding the recovery of tissue damaged through such injuries.

DEFINITIONS

Receptor    A portion of a cell specialized to detect changes in the cell's environment and trigger various actions; it acts as a switch through binding and unbinding of molecules Agonist    A substance which binds to a receptor and changes its function as a result of the binding; it may trigger a cascade of activity within or outside of the cell on which the receptor resides Antagonist    A substance which binds to a receptor without directly altering its function; an antagonist's effects are caused by preventing the binding of, and blocking the biologic actions of, agonist molecules BZ    Benzodiazepine; a group of drugs used as minor tranquilizers, such as diazepam; they act by binding to receptors and triggering a series of responses Peripheral-type Receptor which was originally identified in
BZ receptor non-CNS tissue (i.e., peripheral to the CNS), which binds BZ molecules, but is distinct from those associated with the GRC (central-type BZ receptors)
CNS Central Nervous System; composed of the brain and the spinal cord.
Hypoxia Deficiency of oxygen in body tissues, usually because the blood supplying the tissues has too low a concentration of oxygen, which can be due to: a deficiency of red blood cells, lack of adequate hemoglobin (a molecule which carries oxygen), or insufficient oxygen reaching the blood in the lungs.
Ischemia Inadequate blood flow to a part of the body, caused by constriction or blockage of blood vessels supplying it, or cessation of blood flow.
Trauma Physical insult to the brain and/or other portions of the CNS.

DETAILED DESCRIPTION OF THE INVENTION

This invention provides means for selecting and using compounds that are useful in the treatment of injuries to the CNS, especially head injuries. By binding to the peripheral-type BZ sites, these compounds minimize the extent of damage caused by CNS injury. They can also assist in the recovery from CNS injury.

According to this invention, inhibitory agonists of the peripheral-type BZ receptors reduce damage caused by CNS injury and help healing after CNS injury. Inhibitory agonists are screened for effectiveness by their high binding efficiency to the peripheral-type BZ receptors and their in vivo ability to enhance neurological performance after injury.

One likely mode of action of these inhibitory agonists is by decreasing the levels of cytokine production at the site of injury. The number of macrophages is known to increase at the site of injury. Handschumacher, R. E., "Immunosuppressive agents," in THE PHARMACOLOGICAL BASIS OF THERAPEUTICS, 8th ed. (Gillman, A. G., et al., eds.), Pergamon Press, N.Y., pp. 1264–1276 (1990). Macrophages are known to secrete cytokines such as IL-1 and TNF and to be involved in the cellular immune response. By blocking the cytokine production by these cells at the site of injury, there is a decrease in edema, necrosis, and other damage. Additionally, these cytokines may be involved in feedback stimulation of proliferation of macrophages, so that the inhibitory agonists may also be decreasing the overall number of macrophages at the site of injury.

A possible secondary mode of action of these inhibitory agonists is through inhibition of proliferation of cells with peripheral-type BZ receptors on their surfaces. It has been demonstrated that both glial cells and macrophages have proportionally large numbers of these receptors. Additionally, both types of cells increase in number at sites of trauma and/or ischemia.

Another secondary mode of activity of the inhibitory agonists is through stimulation of glucocorticoid production. It has been shown that glucocorticoids block production of cytokines from macrophages. Handschumacher, R. E., Upra. It has also been shown that a number of the compounds useful in this invention act to stimulate glucocorticoid production. See, e.g., U.S. Pat. No. 5,032,595.

Additionally, as has already been noted, cytokines such as IL-1 cause increases in the number of glial cells. Thus, if macrophages are inhibited by the inhibitory agonists so that lower amounts of IL-1 are produced, the number of glial cells at the site of inhibition will also be held in check, preventing damage that is caused by excessive numbers of such cells.

Therefore, one means for selecting for compounds useful in this invention is to couple binding studies to peripheral-type BZ receptors with measurement of IL-1 production and/or change in number of glial cells. Compounds useful in this invention will have a high affinity for the peripheral-type BZ receptors. Additionally, these compounds will control or decrease the production of IL-1 and/or other cytokines at the site of CNS damage, and the compounds will control or decrease glial cell proliferation at that site.

Another means for selecting for compounds useful in this invention utilizes the first step discussed above: measurement of binding to peripheral-type BZ receptors. In addition, the compounds are tested in vivo for their effects on neurological deficits caused by CNS damage. For example, in vivo analysis can be by way of measurement of grip scores of affected and treated mice, grip times for such mice, and mortality of test animals.

For treatment of injury, the compounds are administered shortly after injury occurs. They can be administered in a variety of manners, including intravenously and intraperitoneally. Due to the fact that victims of CNS injury are often unable to self-administer medication, and are usually in need of immediate treatment, i.v. administration is the preferred method. The compounds of this invention can be supplied to emergency care personnel for administration to a patient as soon after the injury as possible. As demonstrated by the data below in Table 1, at a set dose, the sooner the compounds are administered, the less CNS tissue damage results. However, when the dose of the drug is increased, a longer delay (up to one hour post injury) in initial treatment is tolerated. (Table 1, below) While it would be preferable to pretreat patients to avoid any damage, pre-treatment is impractical.

Administration of these compounds may also reverse damage that has occurred after injury and before treatment.

TABLE 1

EFFECT OF POST-INJURY DELAY IN THE ADMINISTRATION OF PK 11195 ON NEUROLOGICAL DEFICIT SCORES IN MICE 1 mg/kg, i.v.

| POST INJURY TIME (min) | SCORE | |
|---|---|---|
| | Control | Treated |
| 5 | 2.06 ± 0.23 | 3.07 ± 0.47* |
| 30 | 1.54 ± 0.43 | 3.53 ± 0.36** |
| 60 | 2.54 ± 0.51 | 1.93 ± 0.42 |

Significantly different from control score at *P<0.05 and **P<0.004 by the Mann-Whitney U-test.

10 mg/kg. i.v.

| POST INJURY TIME (min) | SCORE | |
|---|---|---|
| | Control | Treated |
| 5 | 2.06 ± 0.23 | 2.89 ± 0.40* |
| 30 | 1.56 ± 0.50 | 2.53 ± 0.40 |
| 60 | 1.38 ± 0.60 | 2.62 ± 0.40** |

Significantly different from control score at *P<0.05 and **P<0.03 by the Mann-Whitney U-test.

In Vitro Screening

One step in selecting compounds that are useful in this invention is in vitro screening for the ability of the compounds to bind to the peripheral-type BZ receptors. This screening can be done with receptors isolated in brain extracts, (Braestrup, C., and Squires, R. F., "Specific benzodiazepine receptors in rat brain characterized by high-affinity [hu 3H]diazepam binding," Proc. Natl. Acad. Sci, USA, 74:3805–3809 (1977)) in non-brain tissue containing peripheral-type BZ receptors (Wang, J. K. T., et al., "Structural requirements for the binding of benzodiazepines to their peripheral-type sites," Mol. Pharmacol. 25:349-351 (1984)), or with receptors cloned and expressed in recombinant cells. Sprengel, R., et al., "Molecular cloning and expression of cDNA encoding a peripheral-type benzodiazepine receptor," J. Biol. Chem., 264:20415–20421 (1989).

The binding affinity of the compounds can be tested by direct binding (Schoemaker, H., et al., "Specific high affinity binding sites for [hu 3H]Ro5 4864 in rat brain and kidney," J. Pharmacol. Exp. Ther., 285:61–69 (1983)) or by indirect binding such as competitive binding. $IC_{50}$ is a measurement of the concentration of a compound necessary to displace 50% of another compound bound to the receptor. In the procedures described below, $IC_{50}$ of compounds measured against binding by PK11195 was measured. PK11195 is a good compound to use in such a binding assay because it has a high degree of affinity to the peripheral-type BZ receptors.

In Vivo Screening

Binding alone does not distinguish between agonists and antagonists of a receptor. Both types of compounds will have relatively strong binding constants. One way to distinguish agonists from antagonists is by in vivo data on the response of a cell after binding to the receptor. An agonist will produce a response, such as a cascade of chemical reactions, which results in either increased or new activity (for a stimulatory agonist) or inhibition of some already occurring cellular activity (for an inhibitory agonist). An antagonist will have a neutral effect on cell activity, but will have the effect of preventing binding of agonists to the same receptor sites.

One method of testing for agonist activity in the compounds useful in this invention is by observing the effect of administering the compounds on neurological deficits that result from CNS damage. Two tests which can be readily performed are observation of grip score and observation of grip time in injured test animals. Another test for agonist activity is for decrease in mortality caused by the CNS injury. Mice can be treated to simulate CNS injury by a variety of methods: they can be deprived of oxygen by administration of KCN (Nauquier, A., et al., Arch. Int. Pharmacodyn., 249:330 (1981)) or by temporary tying-off of the carotid artery (Braughler, J. M. and Lainer, M. J., "The effects of large doses of methylprednisolone on neurologic recovery and survival in the Mongolian gerbil following three hours of unilateral carotid occlusion," CNS Trauma, 3:153–162 (1986)). Alternatively, blows can be administered to the head or the spinal cord of the test animal.

Selection of Useful Compounds

Those compounds which have strong binding affinity to peripheral-type BZ receptors and additionally produce a physiological response in the cells with those receptors are selected as agonists. Compounds with an $IC_{50}$ against [$^3$H] Ro5-4864 of less than 200 nM are especially useful as having strong affinity for the peripheral-type BZ receptors. Those compounds with sufficiently strong binding are then screened for their in vivo effect as described above. Compounds with a statistically significant increase in grip score or grip time, or a statistically significant decrease in mortality, are useful in this invention.

Preparation of the Compounds

For administration to an injured subject, the compounds useful in the invention may be prepared by any suitable technique known in the art or henceforth developed. Table 2 below provides the chemical formulae for a number of compounds useful in this invention. Additionally, some compounds may be obtained from manufacturers, such as Hoffmann-La Roche Drug Co. (Nutley, N.J.). The preparation of a number of the compounds useful in this invention is described in U.S. Pat. No. 3,336,295, incorporated herein by reference.

TABLE 2

Diazepam

| I) | |
|---|---|
| Ro5 6993 | 4',7-Dichloro-1-ethyl-1,3-dihydro-5-phenyl-2H-1,4-benzodiazepin-2-one |
| RoS 4864 | 4',7-Dichloro-1,3-dihydro-1-methyl-5-phenyl-2H-1,4-benzodiazepin-2-one |
| Ro5 6900 | 2',4',7-Trichloro-1,3-dihydro-1-methyl-5-phenyl-2H-1,4-benzodiazepin-2-one |
| Ro5 6945 | 1-Allyl-4',7-dichloro-1,3-dihydro-5-phenyl-2H-1,4-benzodiazepin-2-one |
| Ro5 6669 | 7-Chloro-1,3-dihydro-4'-methoxy-1-methyl-5-phenyl-2H-1,4-benzodiazepin-2-one |
| Ro5 6531 | 4'-Chloro-7-fluoro-1,3-dihydro-1-methyl-5-phenyl-2H-1,4-benzodiazepin-2-one |
| Ro5 6902 | 4',6',7-Trichloro-1,3-dihydro-1-methyl-5-phenyl-2H-1,4-benzodiazepin-2-one |
| Ro5 3448 | 2',7-Dichloro-1,3-dihydro-1-methyl-5-phenyl-2H-1,4-benzodiazepin-2-one |
| Diazepam (Ro5 2807) | 7-Chloro-1,3-dihydro-1-methyl-5-phenyl-2H-1,4-benzodiazepin-2-one |
| Ro7 5520 | 2',6',7-Trichloro-1,3-dihydro-1-methyl-5-phenyl-2H-1,4-benzodiazepin-2-one |
| Ro5 5115 | 4'-Chloro-1,3-dihydro-1-methyl-5-phenyl-2H-1,4-benzodiazepin-2-one |
| R05 4608 | 2'-Chloro-1,3-dihydro-1-methyl-5-phenyl-2H-1,4-benzodiazepin-2-one |
| Ro5 6524 | 4'-Chloro-7-fluoro-1,3-dihydro-1-methyl-5-phenyl-2H-1,4-benzodiazepin-2-one |
| Ro5 5122 | 4'-Fluoro-1,3-dihydro-1-methyl-5-phenyl-2H-1,4-benzodiazepin-2-one |
| Ro5 3464 | 1,3-Dihydro-1-methyl-5-phenyl-2H-1,4-benzodiazepin-2-one |
| II) | |
| PK 11195 | N-methyl-N-1-(1-methyl,propyl)(2-chlorophenyl)-3-isoquinoline carboxamide |
| PK 14105 | 1-(2-fluoro-5-nitrophenyl)-1-methyl-N(1-methyl-propyl)-3-isoquinoline carboxamide |

Administration

For administration according to the invention, the pharmaceutical compositions are prepared in conventional dosage unit forms by incorporating an active compound of the invention or a mixture of such compounds, with a nontoxic pharmaceutical carrier according to accepted procedures in a nontoxic amount sufficient to produce the desired pharmacodynamic activity in a subject, animal or human. Preferably, the composition contains the active ingredient in an active, but nontoxic amount, selected from about 1 mg to about 300 mg of active ingredient per dosage unit. This quantity depends on the specific biological activity desired and the condition of the patient.

The pharmaceutical carrier employed may be, for example, a liquid (see e.g. Remington's Pharmaceutical Sciences, 14th Edition, 1970). Typical liquid carriers are propylene glycol, aqueous solutions of β-cyclodextrins, syrup, peanut oil, and olive oil and the like emulsions. Liquid dosage forms also need pharmaceutically acceptable preservatives and the like.

Dosage units can be prepared for injection, either i.v. or i.p. Thus, they can be packaged in ampules or bottles for retrieval by syringe. They can also be packaged directly in syringes, such as disposable syringes.

The following examples provide evidence of the effectiveness of these compounds in the treatment of CNS injury.

EXAMPLE 1

Binding Assay

The compounds defined in this invention bind to peripheral-type BZ receptors. Table 3 shows the results of binding assays for these compounds. Ro5-4864 is known to bind to the peripheral-type BZ sites, and was used as a control in these binding assays. The binding assay was a competitive assay, measuring the displacement of $^3$H-RO5-4864 in brain homogenates by the compounds being tested. $IC_{50}$ represents the concentration at which 50 percent of the Ro5-4864 is displaced. As can be seen from Table 3, a number of these compounds bind with high affinity to the peripheral-type BZ sites as shown by their low $IC_{50}$ values. Some of these compounds were further tested in in vivo studies.

TABLE 3

RANK ORDER OF POTENCY OF
PERIPHERAL-TYPE BZ SITE COMPOUNDS

| Compound | $IC_{50}$ (nM) |
| --- | --- |
| 1. PK 11195* | 0.57 |
| 2. PK 14105* | 4.5 |
| 3. Ro5-6993# | 6.1 |
| 4. Ro5-4864# | 8.5 |
| 5. Ro5-6900# | 10.0 |
| 6. Ro5-6945# | 14.3 |
| 7. Ro5-6669# | 18.7 |
| 8. Ro5-6902# | 23.4 |
| 9. Ro5-6531* | 33.4 |
| 10. Ro5-3448# | 35.2 |
| 11. Diazepam* | 70 |
| 12. Ro7-5520# | 93.1 |
| 13. Ro5-5115# | 106.5 |
| 14. Ro5-4608# | 214.6 |
| 15. Ro5-6524# | 340 |
| 16. Ro5-5122# | 441.7 |
| 17. Ro5-3464* | 1230 |
| 18. Clonazepam* | 9180 |
| 19. Ro16-6028* | >10,000 |

*Data produced by the procedure described herein.
Data from Wang, J. K. T., et al., "Structural requirements for the binding of benzodiazepines to their peripheral-type sites," Mol. Pharmacol. 25:349–351 (1984).

Two in vivo models of CNS were used to test the efficacy of these compounds. These are physical trauma and brain hypoxia.

EXAMPLE 2

Physical Trauma

A) Methods

Physical trauma was administered to demonstrate the effects of the compounds after compression injury. The following protocol was used:

The compound to be tested was weighed and suspended in a polyethylated castor oil solution ("Cremophore") (21% Cremaphore, 3% ethanol in 0.9% saline). The concentration of the solution was then adjusted for administration at a dose of 0.01 cc/gm body weight. For example, for a dose of 10 mg/Kg, the solution was made 1.0 mg/cc, and a 23 g mouse would receive 0.23 cc of this solution. The solution was sonicated for approximately 90 minutes, or until the compound is dissolved.

Male CF-1 mice (15–25 gm) were weighed and marked for identification purposes. Each individual mouse was restrained by grasping the dorsal skin of the neck until the mouse was still. An impounder was used to administer the trauma. The impounder consists of a weight suspended over the animal's head at a height sufficient to produce significant injury when dropped, and a means for immobilizing the animal (in this case, room to hold the animal in place). An example of such an impounder can be found in Hall, E.D., "High Dose Glucocorticoid Treatment Improves Neurological Recovery in Head Injured Mice," J. Neurosurg. 62:882–887, 883. The mouse was positioned properly under the impounder, and the weight was released from its preset height (11 cm).

Immediately following injury, the mouse was placed under a heat lamp. At various times after injury, the drug was administered intravenously at the specified dose. The time of injury and the time of injection were recorded.

Figure 1:
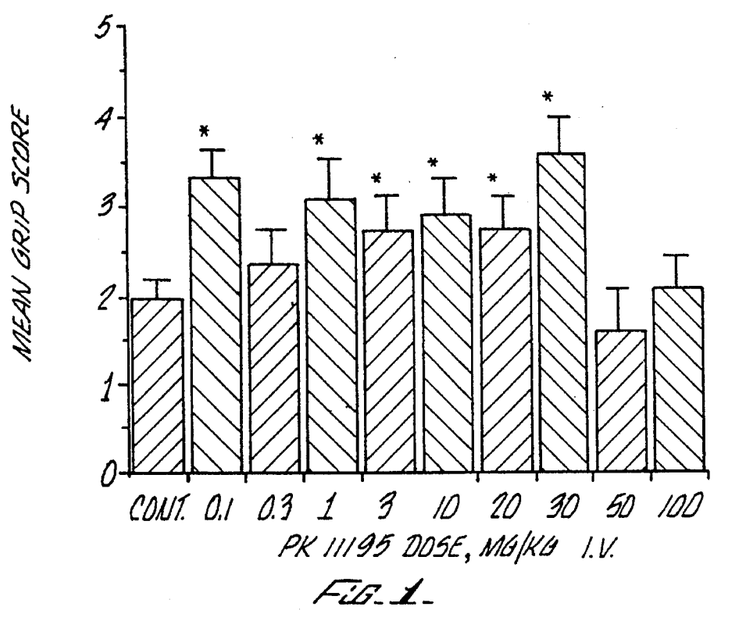
FIG. 1 shows grip scores 18 hours after trauma with or without (i.e., control) subsequent administration of the peripheral-type BZ receptor inhibitory agonist PK11195.

FIGS. 1 through 8 show grip scores measured 18 hours post trauma for several of the compounds. FIG. 1 shows the effectiveness of PK11195 in this model: at very low doses, e.g.., at 0.1 mg/kg, administered i.v., PK11195 in this model: at very low doses, e.g., 0.1 mg/kg, administered i.v., PK11195 causes a statistically significant increase in the grip score. PK1119-5 at 10 mg/kg can be administered up to 1 hour post-injury to produce a statistically significant increase in grip score when compared to controls (see Table 1, above). The number of animals: used at each dose for FIG. 1 were as follows:

| dose | number of animals |
| --- | --- |
| control | 104 |
| 0.1 mg/kg | 30 |
| 0.3 mg/kg | 23 |
| 1.0 mg/kg | 15 |
| 3.0 mg/kg | 18 |
| 10 mg/kg | 19 |
| 20 mg/kg | 15 |
| 30 mg/kg | 14 |
| 50 mg/kg | 7 |
| 100 mg/kg | 16 |

Figure 2:
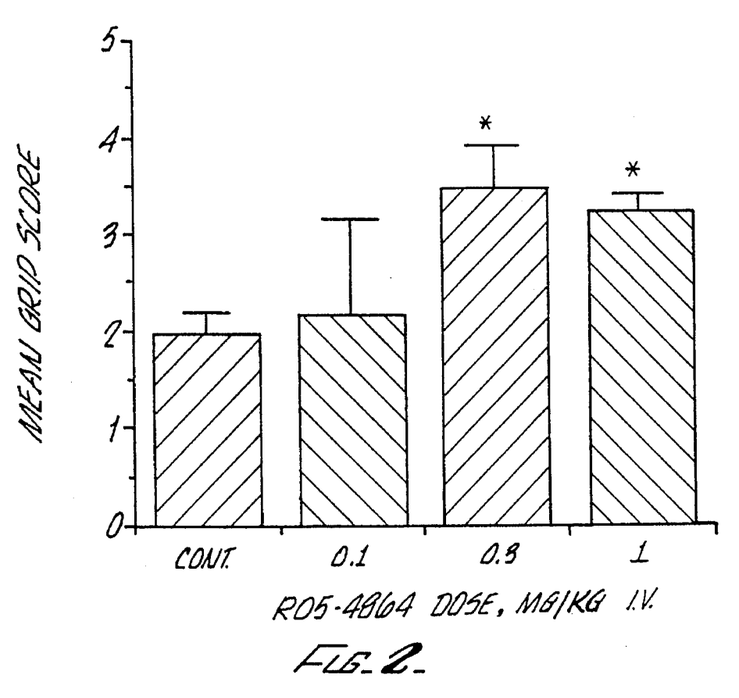
FIG. 2 shows grip scores 18 hours after trauma with or without (i.e., control) subsequent administration of the peripheral-type BZ receptor inhibitory agonist Ro5-4864.

Other effective compounds are shown in the following FIGS. 2–4. FIG. 2 shows Ro5-4864 using the following number of animals:

| dose | number of animals |
| --- | --- |
| control | 104 |
| 0.1 mg/kg | 6 |
| 0.3 mg/kg | 14 |
| 1.0 mg/kg | 6 |

Figure 3:
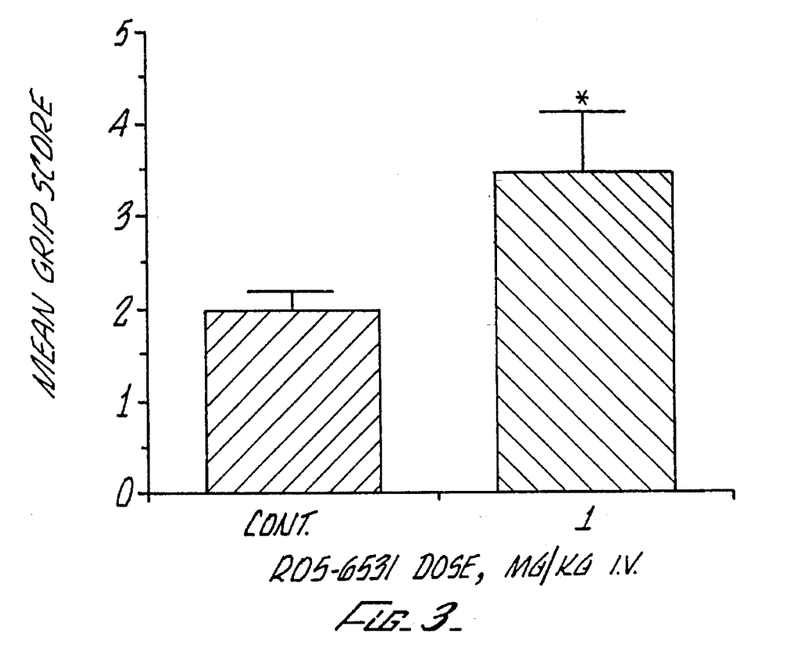
FIG. 3 shows grip scores 18 hours after trauma with or without (i.e., control) subsequent administration of the peripheral-type BZ receptor inhibitory agonist Ro5-6531.

FIG. 3 shows Ro5-6531, using the following number of animals:

| dose | number of animals |
|---|---|
| control | 104 |
| 1.0 mg/kg | 7 |

Figure 4:
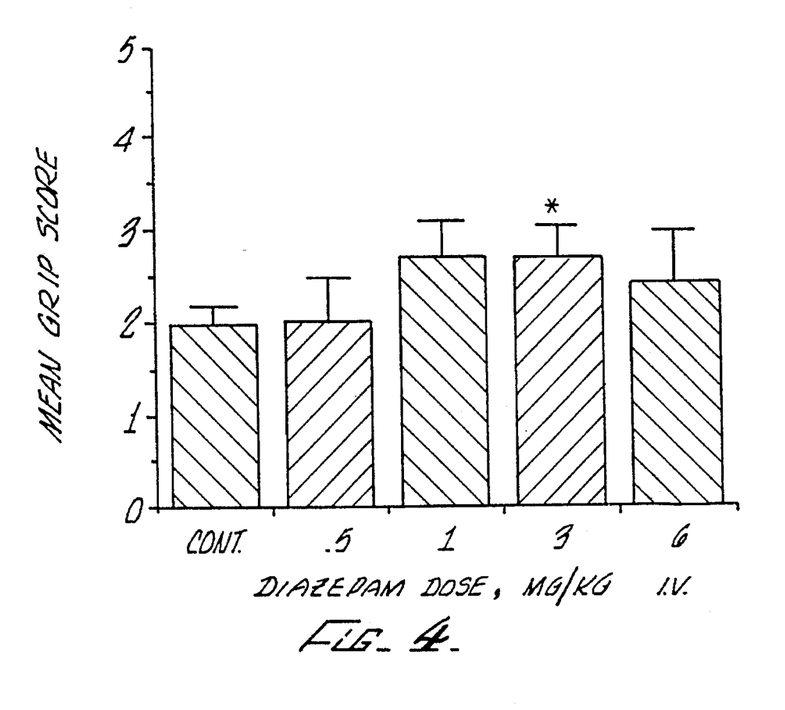
FIG. 4 shows grip scores 18 hours after trauma with or without (i.e., control) subsequent administration of the peripheral-type BZ receptor inhibitory agonist Diazepam.

FIG. 4 shows diazepam, using the following number of animals:

| dose | number of animals |
|---|---|
| control | 104 |
| 0.5 mg/kg | 9 |
| 1.0 mg/kg | 16 |
| 3.0 mg/kg | 19 |
| 6.0 mg/kg | 12 |

Figure 5:
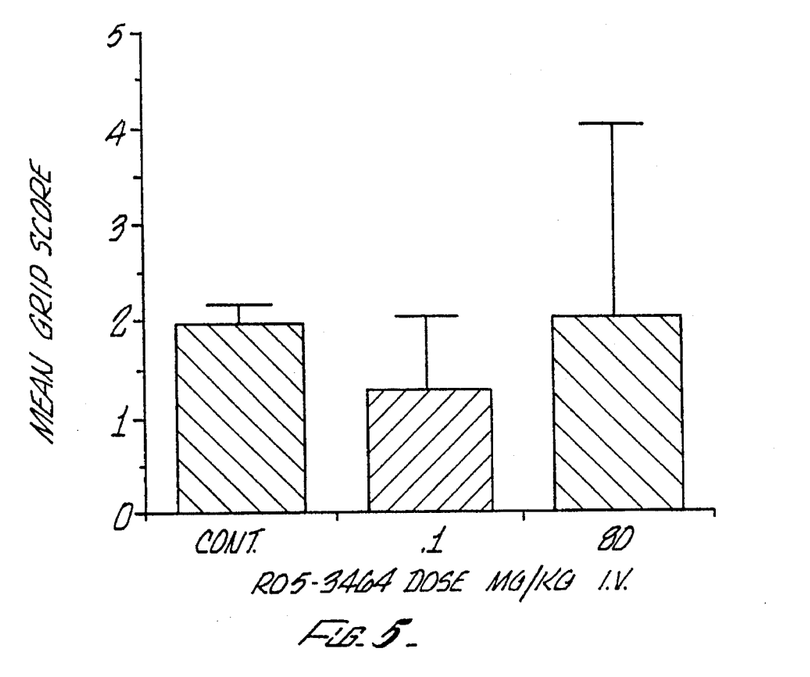
FIG. 5 shows grip scores 18 hours after trauma with or without (i.e., control) subsequent administration of the compound Ro5-3464.

Compounds found to be non-effective are shown in the following FIGS. 5–8. FIG. 5 shows Ro5-3464, using the following number of animals:

| dose | number of animals |
|---|---|
| control | 104 |
| 0.1 mg/kg | 7 |
| 80 mg/kg | 2 |

Figure 6:
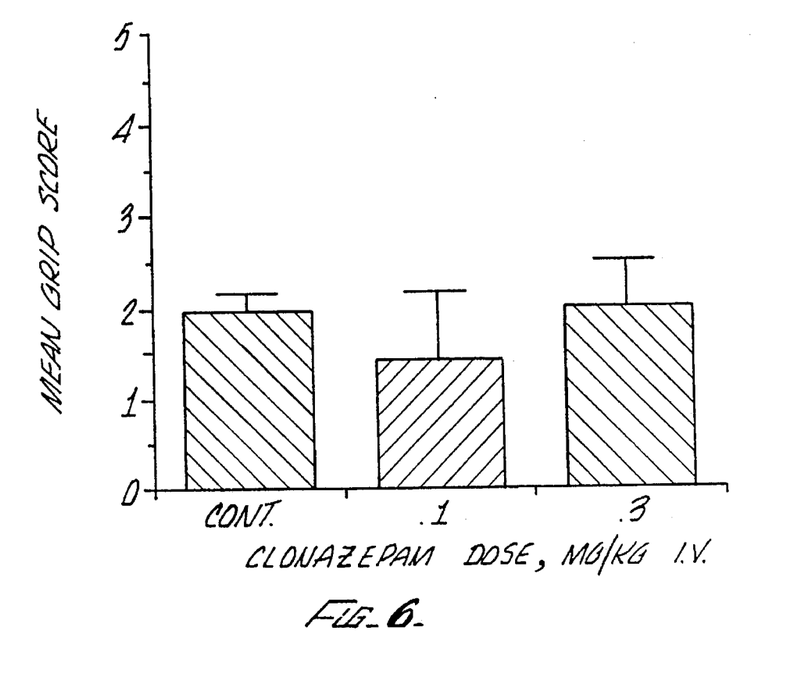
FIG. 6 shows grip scores 18 hours after trauma with or without (i.e., control) subsequent administration of the compound Clonazepam.

FIG. 6 shows clonazepam, using the following number of animals:

| dose | number of animals |
|---|---|
| control | 104 |
| 0.1 mg/kg | 7 |
| 0.3 mg/kg | 12 |

Figure 7:
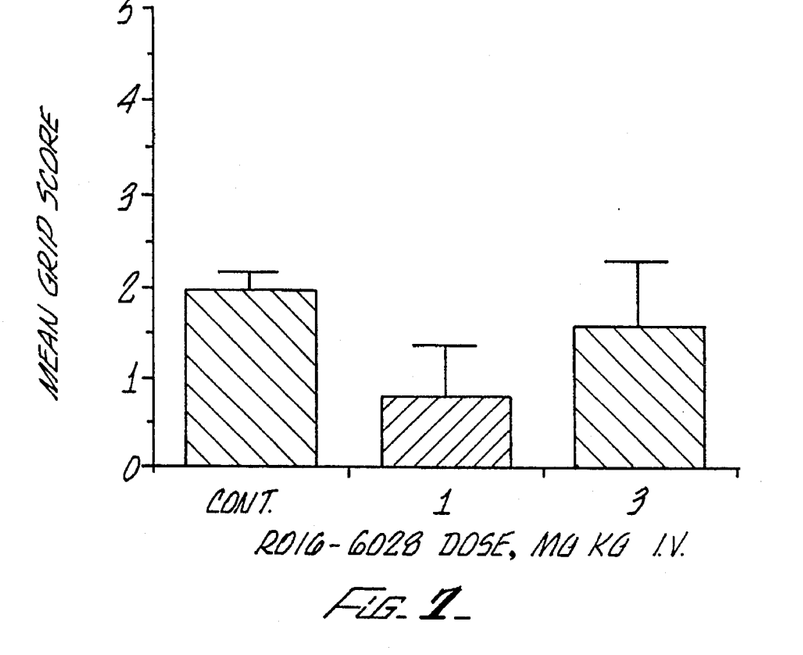
FIG. 7 shows grip scores 18 hours after trauma with or without (i.e., control) subsequent administration of the compound Ro16-6028.

FIG. 7 shows Ro16-6028, using the following number of animals:

| dose | number of animals |
|---|---|
| control | 104 |
| 1.0 mg/kg | 5 |
| 3.0 mg/kg | 7 |

Figure 8:
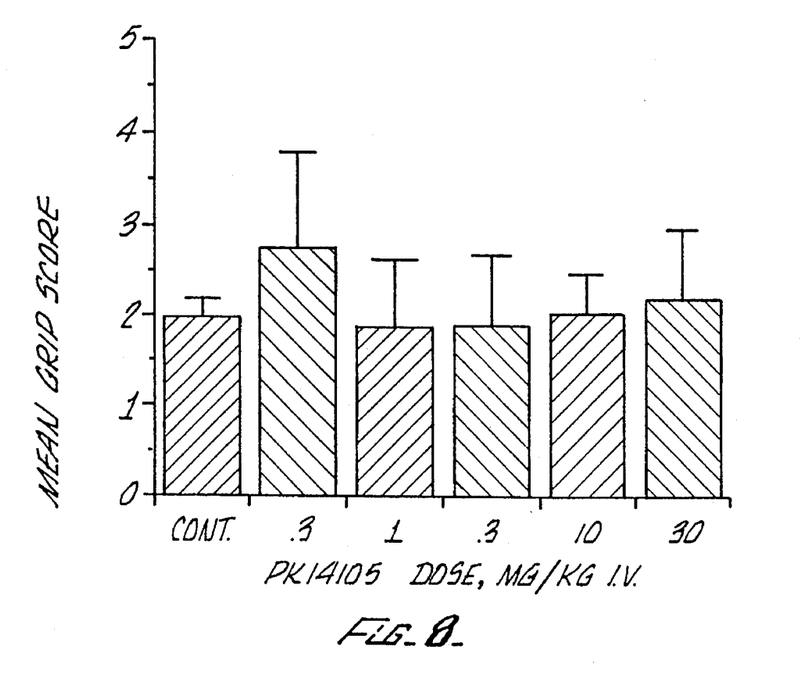
FIG. 8 shows grip scores 18 hours after trauma with. or without (i.e., control) subsequent administration of the peripheral-type BZ receptor antagonist PK14105.

FIG. 8 shows PK14105, using the following number of animals:

| dose | number of animals |
|---|---|
| control | 104 |
| 0.3 mg/kg | 4 |
| 1.0 mg/kg | 7 |
| 3.0 mg/kg | 7 |
| 10 mg/kg | 8 |
| 30 mg/kg | 6 |

B) Measurement of Grip Score

Each mouse was evaluated 18 hours post-injury for neurological deficit. The delay of 18 hours provided time for any sedative effects of the compound to wear off. It also provided time for healing to occur. Mortality was also noted. A standard grip test, as described in Hall et al., J. Neurosurg. 68:456–461 (1988), was used. The apparatus consisted of a taut string suspended between two uprights, 60 cm in length and 40 cm above a padded table.

Each mouse was picked up by the tail and placed on the string. Care was taken that both front paws came in contact with the string, ensuring that each mouse had an equal opportunity to grasp the string. The tail was then released. Grip score was recorded based on the mouse's performance while on the string. The following criteria were used (taken from Hall, E. D., J. Neurosurg. 62:882–887 (1985)):

| Score | Criteria |
|---|---|
| 0 | Fell off string within the 30 second period |
| 1 | Held on in some way for 30 seconds |
| 2 | Held on for 30 seconds and got 4 paws on the string for at least 5 seconds |
| 3 | Held on for 30 seconds, getting 4 paws and the tail wrapped on the string for at least 5 seconds |
| 4 | Held on with 4 paws and tail and traveled along the string for at least 5 seconds |
| 5 | Traveled along the string and reached one of the uprights within 30 seconds. |

C) Statistical Analysis Results of the above test were analyzed for statistical significance using the Mann-Whitney U test. See R. V. Tallarida & R. B. Murray, MANUAL OF PHARMACOLOGIC CALCULATIONS WITH COMPUTER PROGRAMS, Springer-Verlag, N.Y., pp. 57–59 (1981). This test was used to compare each set of grip scores for a particular dose of a particular compound against the grip scores for the control group. FIGS. 1 through 8 illustrate the 18 hour mean grip scores for a variety of compounds. Mean grip scores that were significantly different from the control scores based on the Mann-Whitney U-test, i.e., are statistically significant, are starred (*).

D) Rank Order of Efficacy

Figure 9:
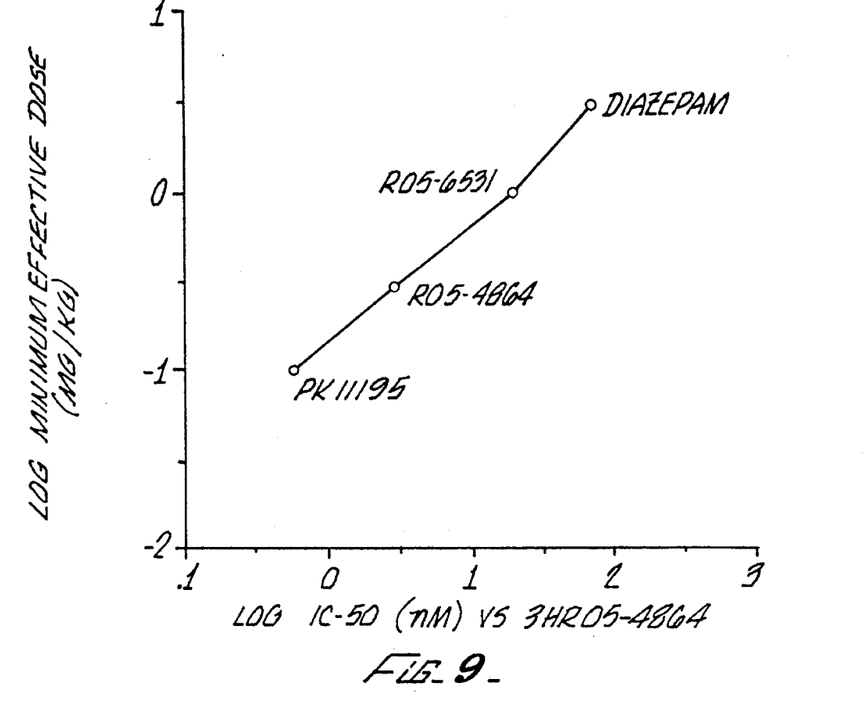
FIG. 9 shows the correlation between minimum effective dose of the peripheral-type BZ receptor inhibitory agonist and $IC_{50}$.

FIG. 9 shows the correlation between the in vitro binding assay data and the in vivo grip score data. There is a remarkable correlation between $IC_{50}$ and log of the minimum dose effective in vivo. The stronger the binding of the compound in vitro to brain homogenates, the lower the minimum effective dose. Thus, PK11195, Ro5-4864, Ro5-6531 and diazepam have been demonstrated as effective compounds for the treatment of CNS trauma or disease. Additionally, by extrapolation, for example using the data in Table 3, other agonists of the peripheral-type BZ receptors are also effective for the treatment of CNS trauma or disease. Examples of some such compounds are Ro5-6993, Ro5-6900, Ro5-6945, Ro5-6669, Ro5-6902, and Ro5-3448.

In contrast, Ro5-3464, clonazepam, and Ro16-6028 have very high $IC_{50}$ values, and are inactive in the treatment of CNS damage (see FIGS. 5–7).

E) Receptor Antagonists

Antagonists to the peripheral-type BZ receptor are not effective in treating CNS damage. Antagonists bind to the receptor with high affinity, but do not trigger the same functions as the binding of agonists. Instead, they block the binding of agonists.

PK14105 was studied in vitro using the procedures above to analyze $IC_{50}$ values in competition with Ro5-4864. As can be seen from Table 3, PK14105 has a very strong binding affinity to the peripheral-type BZ receptor.

PK14105 was also administered to animals using the above described in vivo tests. As can be seen from FIG. 8, this compound is inactive in treating CNS damage. At both moderate and high doses, the grip scores of the animals stay the same as those of the controls. Thus, it is an antagonist to the peripheral-type BZ receptor.

Table 4 below shows the effects on grip score when the antagonist PK14105 is administered in conjunction with an inhibitory antagonist. The antagonist alone has no statistically significant effect on grip score post trauma (row 3 as compared to row 1). The inhibitory agonist alone does (row 2 as compared to row 1). When both the antagonist and the inhibitory agonist are administered together, at 1 hour posttrauma the antagonist prevents the agonist from improving grip score (row 4).

TABLE 4

ANTAGONISM OF Ro5 4864-INDUCED IMPROVEMENT OF GRIP SCORE BY PK 14105 FOLLOWING HEAD-INJURY IN MICE

| PREINJURY TREATMENT[a] | POSTINJURY TREATMENT[b] | GRIP TEST SCORE[c] |
|---|---|---|
| Vehicle | Vehicle | 1.13 ± 0.27 |
| Vehicle | 0.3 mg/kg Ro5 4864 | 1.84 ± 0.24* |
| 10 mg/kg PK 14105 | Vehicle | 1.40 ± 0.28 |
| 10 mg/kg PK 14104 | 0.3 mg/kg Ro5 4864 | 0.93 ± 0.21 |

[a]Animals were administered vehicle or PK 14105 i.v. 30 min prior to head injury.
[b]Animals were administered vehicle or Ro5 4864 i.v. 5 min after head injury.
[c]Animals were tested 1 hour after head-injury
*Significantly different from vehicle pre- and postinjury treatment group at *P<0.05 by the Mann-Whitney U-test

EXAMPLE 3

Brain Hypoxia

Brain hypoxia was produced by administration of KCN. The following protocol was used:

A) Methods

The compound to be tested was weighed and suspended in a Cremophore solution (21% Cremaphore, 3% ethanol in 0.9% saline). The solution was prepared for injection using a volume of 0.01 cc/gm body weight. For example, for a 10 mg/Kg dose, a 1 mg/cc solution was made and 0.23 cc was administered to a 23 g mouse. The solution was sonicated for approximately 90 minutes, or until the compound was dissolved.

Male CF-1 mice (15–25gm) were weighed and marked for identification purposes. For i.v. administration each mouse was placed under a heat lamp. Each mouse was injected with the desired dose of the indicated test compound.

After the indicated time period (usually 15 to 30 min.) various doses of potassium cyanide (KCN) were administered i.v.

The times of the pretreatment injection and the KCN injection were recorded. Mice were then observed in a padded box for lethality of the KCN dose. Results were expressed as percent lethality or percent survival.

B) Results

Figure 10:
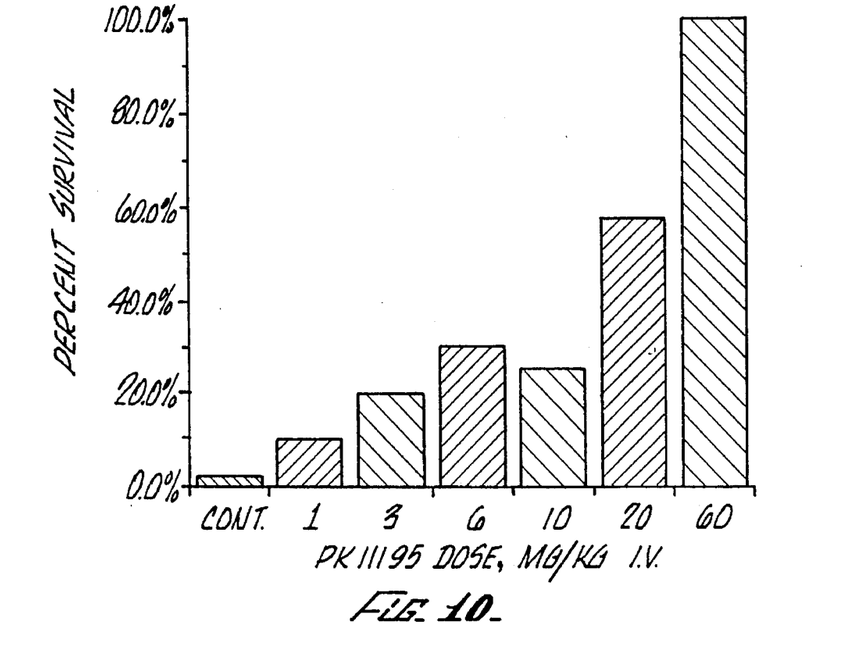
FIG. 10 shows percent survival using various doses of PK11195 after induction of brain hypoxia.
Figure 11:
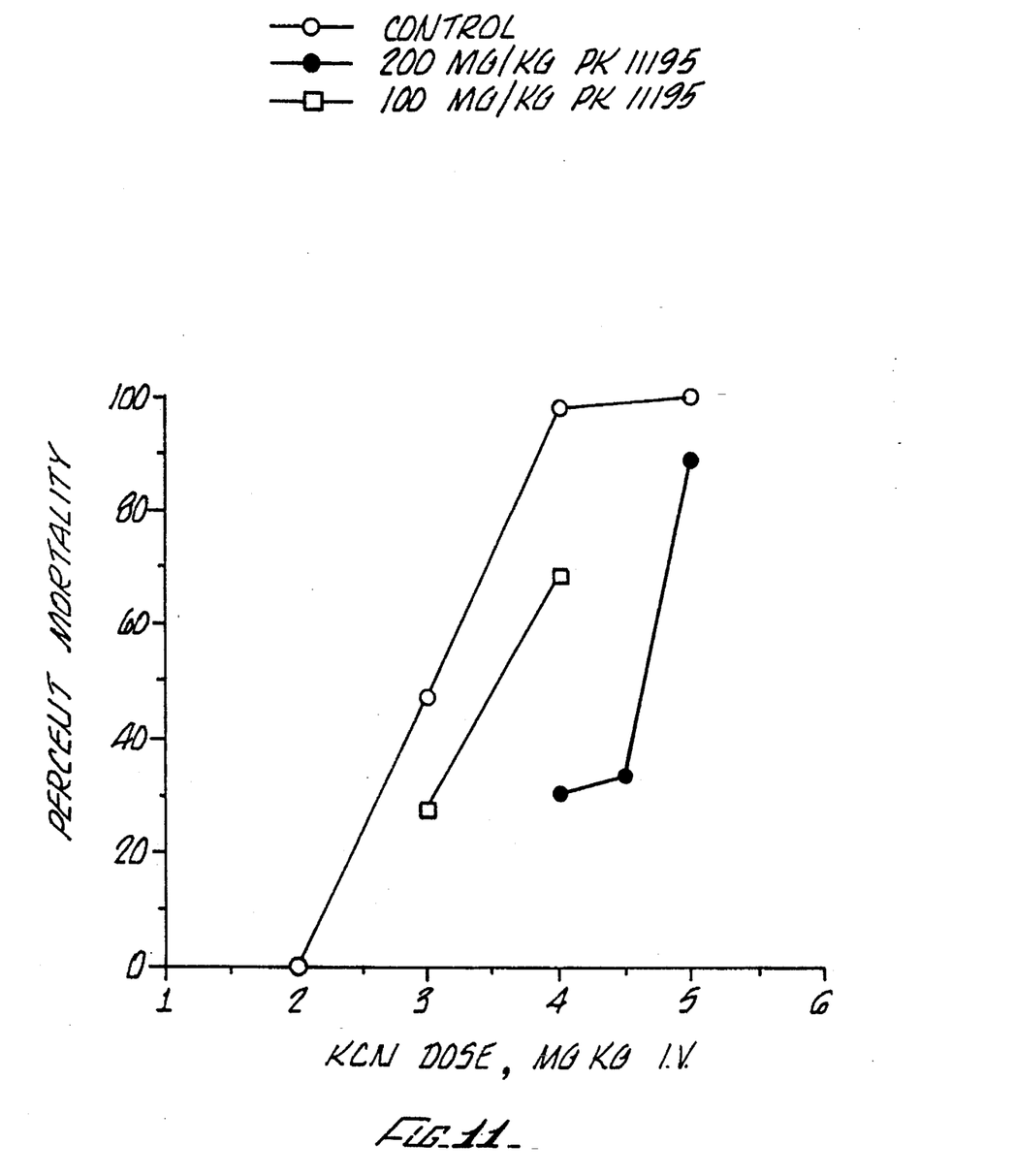
FIG. 11 shows percent mortality when KCN dose is varied prior to administration of PK11195.

PK11195 was tested in the hypoxia model. Percent survival after administration of both the KCN and the compound was analyzed. FIGS. 10 and 11 show two difference analyses of the data. FIG. 10 shows a bar graph of percent survival as correlated with change in dose of PK11195 administered. As can be seen, increasing the dose of the compound increases the percent survival. FIG. 11 shows that at set concentrations of PK11195 increasing the KCN dose will decrease survival and increase mortality. In addition, this figure shows that increased levels of PK11195 protect against higher doses of KCN. Thus, FIGS. 10 and 11 show that there is a direct in vivo effect of the compounds of this invention on survivability after KCN-induced brain ischemia.

The preferred embodiments of this invention have been described and illustrated by the Examples herein. However, it is to be understood that the present invention is not limited by these Examples, which are for purposes of illustration. The invention is only limited by the terms of the following claims.

I claim:

1. A method for treatment of central nervous system damage in a mammal which damage is associated with inflammation comprising:

administering, to a mammal suffering from central nervous system damage associated with inflammation, an amount of a peripheral-type BZ receptor inhibitory agonist effective to minimize or prevent further central nervous system damage;

wherein said inhibitory agonist binds to peripheral-type BZ receptors in a competitive assay with labeled Ro5-4864 with an $IC_{50}$ of at most 200 nM, with the proviso that said agonist is not diazepam.

2. The method of claim 1 wherein the peripheral-type BZ receptor inhibitory agonist is a compound selected from the group consisting of PK11195, Ro5-4864, Ro5-6531, Ro5-6993, Ro5-6900, Ro5-6945, Ro5-6669, Ro5-6902, Ro5-3448, Ro7-5520 and Ro5-5115.

3. A method for treatment of central nervous system damage associated with inflammation caused by trauma to the head of a mammal comprising:

administering, to a mammal suffering from central nervous system damage associated with inflammation caused by trauma to the head, an amount of a peripheral-type BZ receptor inhibitory agonist effective to minimize or prevent further central nervous system damage.

4. The method of claim 3 wherein said peripheral-type BZ receptor inhibitory agonist binds to peripheral-type BZ receptors in a competitive assay with labelled Ro5-4864 with an $IC_{50}$ of at most 200 nM.

5. The method of claim 3 wherein the peripheral-type BZ receptor inhibitory agonist is a compound selected from the group consisting of PK11195, Ro5-4864, Ro5-6531, diazepam, Ro5-6993, Ro5-6900, Ro5-6945, Ro5-6669, Ro5-6902, Ro5-3448, Ro7-5520 and Ro5-5115.

6. The method of claim 5 wherein said peripheral-type BZ receptor inhibitory agonist is PK11195.

7. A method for treatment of central nervous system damage caused by brain ischemia in a mammal comprising:

administering, to a mammal suffering from central nervous system damage caused by brain ischemia, an amount of a peripheral-type BZ receptor inhibitory agonist effective to minimize or prevent further central nervous system damage, with the proviso that said agonist is not diazepam.

8. The method of claim 7 wherein said central nervous system damage is associated with inflammation.

9. The method of claim 7 wherein said peripheral-type BZ receptor inhibitory agonist binds to peripheral-type BZ receptors in a competitive assay with labelled Ro5-4864 with an $IC_{50}$ of at most 200 nM.

10. The method of claim 7 wherein said peripheral-type BZ receptor inhibitory agonist is a compound selected from the group consisting of PK11195, Ro5-4864, Ro5-6531, Ro5-6993, Ro5-6900, Ro5-6945, Ro5-6669, Ro5-6902, Ro5-3448, Ro7-5520 and Ro5-5115.

11. The method of claim 10 wherein said peripheral-type BZ receptor inhibitory agonist is PK11195.

12. A method for treatment of central nervous system damage associated with inflammation caused by hypoxia comprising:

administering, to a mammal suffering from central nervous system damage associated with inflammation caused by hypoxia, an amount of a peripheral-type BZ receptor inhibitory agonist effective to minimize or prevent further central nervous system damage;

wherein said peripheral-type BZ receptor inhibitory agonist binds to peripheral-type BZ receptors in a competitive assay with labeled Ro5-4864 with an $IC_{50}$ of at most 200 nM with the proviso that said agonist is not diazepam.

13. The method of claim 12 wherein said peripheral-type BZ receptor inhibitory agonist is a compound selected from the group consisting of PK11195, Ro5-4864, Ro5-6531, Ro5-6993, Ro5-6900, Ro5-6945, Ro5-6669, Ro5-6902, Ro5-3448, Ro7-5520 and Ro5-5115.

14. The method of claim 13 wherein said peripheral-type BZ receptor inhibitory agonist is PK11195.

15. A method for treatment of central nervous system damage in a mammal which damage is associated with inflammation caused by trauma to the head comprising: administering to said mammal an amount of PK11195 effective to minimize or prevent further central nervous system damage.

* * * * *